United States Patent
Stimson

(10) Patent No.: US 9,522,173 B2
(45) Date of Patent: Dec. 20, 2016

(54) COMPOSITIONS AND METHODS RELATING TO THE TREATMENT OF DISEASES INVOLVING TH1 AND TH2/TH17

(71) Applicant: ALFACYTE, Ltd., Milngavie, Glasgow (GB)

(72) Inventor: William Stimson, Glasgow (GB)

(73) Assignee: ALFACYTE LTD., Glasgow (GB)

( * ) Notice: Subject to any disclaimer, the term of this patent is extended or adjusted under 35 U.S.C. 154(b) by 0 days.

(21) Appl. No.: 14/426,197

(22) PCT Filed: Sep. 4, 2013

(86) PCT No.: PCT/GB2013/052316
§ 371 (c)(1),
(2) Date: Mar. 5, 2015

(87) PCT Pub. No.: WO2014/037717
PCT Pub. Date: Mar. 13, 2014

(65) Prior Publication Data
US 2015/0209410 A1    Jul. 30, 2015

(30) Foreign Application Priority Data

Sep. 5, 2012 (GB) .................................. 1215873.9

(51) Int. Cl.
*A61K 38/21* (2006.01)
*A61K 39/35* (2006.01)
*A61K 39/39* (2006.01)
*A61K 39/00* (2006.01)

(52) U.S. Cl.
CPC ............. *A61K 38/212* (2013.01); *A61K 39/35* (2013.01); *A61K 39/39* (2013.01); *A61K 2039/542* (2013.01); *A61K 2039/55522* (2013.01); *A61K 2039/57* (2013.01); *A61K 2039/577* (2013.01)

(58) Field of Classification Search
CPC ...... A61K 38/212; A61K 39/35; A61K 39/39; A61K 2039/542; A61K 2039/55522; A61K 2039/57; A61K 2039/577
See application file for complete search history.

(56) References Cited

U.S. PATENT DOCUMENTS 6,350,589 B1    2/2002 Morris et al.

FOREIGN PATENT DOCUMENTS

WO    9524212 A1    9/1995
WO    2005123112 A2    12/2005

OTHER PUBLICATIONS

International Search Report and Written Opinion dated Feb. 18, 2014 for PCT/GB2013/052316.
Souillet, G., F. Rousset, and J. E. de Vries. "Alpha-interferon treatment of patient with hyper IgE syndrome." Lancet 1.8651 (1989): 1384-1384.
Tilg, H. "New insights into the mechanisms of interferon alfa: an immunoregulatory and anti-inflammatory cytokine." Gastroenterology 112.3 (1997): 1017-1021.

*Primary Examiner* — Robert Landsman
(74) *Attorney, Agent, or Firm* — Abel Law Group, LLP

(57) ABSTRACT

A method is provided for the treatment and/or prophylaxis of a condition where an enhancement of a Th1-mediated immune response and suppression of a Th2/Th17-mediated immune response are desired. The method comprises the step of administering to a subject in need thereof a therapeutically effective amount of at least one interferon alpha subtype selected from IFN-α10, IFN-α14, and a hybrid thereof. The condition to be treated may be selected from the group consisting of an autoimmune disease, an inflammatory disease (e.g. inflammatory bowel disease) and allergy or an associated allergic condition.

28 Claims, 8 Drawing Sheets

COMPOSITIONS AND METHODS RELATING TO THE TREATMENT OF DISEASES INVOLVING TH1 AND TH2/TH17

FIELD OF THE INVENTION

The present invention relates to compositions and methods for promoting the induction of a cell-mediated immune response (such as that mediated by Th1 cells) and the suppression of a humoral or allergic immune response (such as that mediated by Th2 and Th17 cells). In particular, the invention relates to compositions and methods for preventing or treating allergy, such as food allergy, and associated allergic diseases, and conditions where an exaggerated Th17 response plays a detrimental role. The invention further extends to the use of the compositions of the invention in the treatment and/or prophylaxis of allergy and associated allergic diseases.

BACKGROUND TO THE INVENTION

Cytokines are immunomodulatory proteins that mediate immune system activation and responses, such as cell-mediated immunity and allergic type humoral responses. T lymphocytes (T cells), which are a major source of cytokines, possess antigen-specific receptors (the T cell receptor) on their cell surface, which allows recognition of foreign antigens. There are two main subsets of T lymphocytes, these being distinguished by the presence of cell surface markers known as CD4 and CD8. T lymphocytes expressing CD4 are also known as helper T cells, and these are regarded as being the most prolific cytokine producers. This subset can be further subdivided into Th1 cells and Th2/T17 cells, and the cytokines they produce are known as Th1-type cytokines and Th2/Th17-type cytokines respectively.

Th1 cells are characterized by the production of pro-inflammatory cytokines such as IFN-γ, IL-2, and TNF-β. Th1 cells are involved in cell-mediated immunity (CMI), this being the immune response typically mounted against viruses and intracellular pathogens. The cell-mediated response also eliminates cancerous cells and stimulates delayed-type hypersensitivity (DTH) skin reactions.

Th2 cells are characterized by the production of Interleukin-4 (IL-4), Interleukin-5 (IL-5), Interleukin-9 (IL-9), Interleukin-10 (IL-10) and Interleukin-13 (IL-13). Th2 cells are thought to play a role in allergy responses. Cytokines such as IL-4 generally stimulate the production of antibodies (the so called "humoral immune response") directed towards extracellular organisms, such as parasites. IL-5 stimulates eosinophil responses, also part of the immune response toward large extracellular parasites.

Th17 cells secrete IL-17 and are involved in immune regulation in cancer and allergic reactions. Functionally, Th17 cells play a role in host defence against extracellular pathogens by mediating the recruitment of neutrophils and macrophages to infected tissues. They are, therefore, largely part of the humoral response together with Th2 cells. Identification of the Th17 family of effector T cells represented a major recent breakthrough. The IL-17 cytokine family is a group of cytokines including IL-17A, B, C, D, IL-17E (IL-25) and IL-17F. It is increasingly recognized that besides T cells, other cells such as NK cells and neutrophils might also be an important source of IL-17. Besides IL-17A, the major cytokine produced by Th17 cells, these cells also release IL-17F, IL-21 and IL-22.

It is hypothesised that in certain circumstances, the Th1 response or the Th2/Th17 response can cause disease. An over-reactive Th1 response can generate organ-specific autoimmune disease such as arthritis, multiple sclerosis, or Type I diabetes, while an over-reactive Th2/Th17 response may underlie allergy and atrophy. It is currently believed that Th17 cells play a major role in host defence against pathogens and an exaggerated Th17 response may lead to severe inflammatory responses and autoimmune diseases—inflammatory bowel diseases (IBD), namely, ulcerative colitis (UC) and Crohn's disease (CD), are chronic inflammatory processes of the gastrointestinal tract. In these diseases a disturbed and exaggerated immune response, mainly towards the endogenous microflora, plays a major role. IL-17 expression is increased in both UC and CD. Type I IFNs have been studied in clinical trials in patients with UC and demonstrated efficacy in selected studies. As anti-viral cytokines, it is now known that Type I IFNs can regulate the development of Th17 cells.

Either a Th1 response or a Th2/Th17 response can down-regulate the other and this is the basis for the so-called "Th1/Th2" hypothesis whereby an immune response may be skewed down either the Th1 or Th2/Th17 route, this being driven by the cytokine profile secreted by one cell group which may promote expansion of that cell type and restrict expansion of the opposing cell type.

Interferons (IFNs) are a family of proteins which are pleiotropic effectors of the immune system. Interferons may be classified into three distinct types—Type I interferons, Type II interferons and Type III interferons. Type I IFNs represent a family of highly homologous cytokines that have been found to activate a range of physiological responses, including anti-viral and anti-proliferative activities as well as playing an important role as activator of the immune response.

Type I interferons consist of interferon alpha (IFN-α), interferon beta (IFN-β), interferon kappa (IFN-κ), interferon tau (IFN-τ), interferon nu (IFN-ν) and interferon omega (IFN-ω). IFN-α is represented in the genome by 13 genes (12 subtypes), some of which have allelic variants and the different IFN-α gene products are called subtypes. All interferon subtypes consist of 166 amino acids stabilised by two disulfide bonds, except for IFN-α2 which has one amino acid less. The homology to mouse IFN-α is 40%.

There are 2 forms of IFN-α: (i) recombinant IFN-alphas which are designated IFN-α2a and IFN-α2b, with only one amino acid difference (IFN-α2a was cloned from a tumour cell line and occurs as a polymorphic variant in human populations); and (ii) a multi-subtype IFN-α, sometimes called natural IFN-alpha, which is expressed from the leukocyte fraction of human blood challenged with Sendai virus or produced by cell lines e.g lymphoblastoid. This product is highly purified with a final immunoaffinity step and contains six major subtypes, namely, IFN-α1, IFN-α2, IFN-α8, IFN-α10, IFN-α14, and IFN-α21, the first two being the major components.

It is known that different pathogens induce different IFN-α subtypes in vitro and that IFN-α subtypes have different antiviral activities. Infection via a variety of routes, including orally, has been shown to induce different subtype profiles. IFN-α subtypes bind to the same receptor, activate common signaling pathways and are expected to have the same biological functions. Similar to many cytokines, two of the natural IFN-α subtypes are glycosylated. IFN-α14 has N-linked glycosylation, while IFN-α2 has O-linked glycosylation. Glycosylation influences the structure and the polarisation of the molecule, but no effects have been demonstrated on receptor binding or direct physiological function. Nevertheless, glycosylation could modulate recognition by the immune system or increase the half-life in the circulation.

All IFN-α subtypes have anti-viral activities, by definition, although their absolute efficacy in this context may vary considerably. In addition, many other biological properties have been described, but with varying potencies, including immunomodulatory and anti-proliferative activities. The pleiotropic effects appear to be due to differential interaction with the receptor chains and signaling through different intracellular pathways to an array of effector molecules.

Overall, IFN-α is part of innate immunity with strong links into adaptive immunity. Both T and B-cells are activated. IFN-α promotes the induction of a Th1 immune response, one mechanism being possibly through the enhancement of IFN-α-inducible protein-10 (IP-10) expression in dendritic cells. Few studies deal with the role of subtypes in T helper-regulation while the cytolytic activity of both T-cells and NK-cells is enhanced.

IFN-α may have a key role in the regulation of the Th1 response. It has been shown that IFN-α treatment promotes Th1 cell differentiation indirectly (largely via IFN-γ), but also appears to suppress Th2 cell development through the suppression of IL-4 and IL-13 gene expression. IFN-α therefore is able to re-establish a Th1/Th2 population balance in diseases and infections that promote a Th2 cell imbalance. In recent years, it became evident that besides its anti-viral effects, several immunomodulatory functions are exerted by IFN-α. IFN-α can impact on dendritic cell differentiation and controls the expression of various pro-inflammatory cytokines such as IL-8 or IL-18 and induces several anti-inflammatory mediators such as IL-1 receptor antagonist (IL-1Ra), soluble TNF receptor p55, IL-10 and IL-18 binding protein. However, the mechanisms of actions of IFN-α are still only partly understood.

In patients with allergy or allergic disease, a Th2-predominant immune response is generated. Th2 cells secrete IL-4 and IL-13 driving B cells to produce Immunoglobulin E (IgE) antibodies specific to an allergen. An allergen is an antigen capable of stimulating a type-I hypersensitivity reaction in atopic individuals mainly through Immunoglobulin E (IgE)-mediated responses. Following that, IgE binds to its high affinity receptor on mast cells, skin cells and mucosal tissues. Upon exposure to the allergen, mast cells release their contents, which include histamine, leukotrienes and prostaglandins. This causes allergic symptoms including, but not limited to, red eyes, itchiness, runny nose, eczema, urticaria, angiodema, shortness of breath, wheezing, coughing, an asthma attack, abdominal pain, vomiting, diarrhoea or even anaphylaxis.

Allergic diseases are among the most common form of chronic illness. The World Health Organisation estimates that over 20 percent of the world population is affected and Europe alone has over 80 million sufferers (Global Allergy and Asthma European Network, 2008). An allergic reaction is usually caused by hypersensitivity of the immune system to an allergen, causing a misdirected immune response. Mild allergies, such as hay fever, are very common in the human population. Severe allergies can be caused by dietary allergens, such as food, by environmental allergens, such as the venom of stinging insects, by medication or can be genetically determined.

Food allergy is a major health concern which is estimated to affect around 6% of young children and 3-4% of adults in Western societies. Food allergy is hypothesised to result from a breakdown in oral tolerance to ingested antigens or allergens. Food allergies and associated allergic diseases include, but are not limited to, dairy (milk) allergy, including Heiner syndrome, egg allergy, soya allergy, fish (shellfish) allergy, peanut and tree nut allergy, sesame and other seed allergy, gluten (wheat) and grains allergy, fruit and vegetable allergy, caffeine allergy, oral allergy syndrome, alcohol allergy, pollen food allergy syndrome, eosinophilic gastroenteritis, IgE mediated gastrointestinal food allergy and C1 esterase deficiency.

Management and treatment of allergic disease is usually via three general approaches: (i) avoidance of the allergen; (ii) medications that target disease symptoms and (iii) conventional immunotherapy, known as desensitisation, which aims to enhance the Th1 response in established disease. However, these approaches are far from ideal. Avoidance of allergens is not always possible, medications that target disease symptoms, such as anti-histamines, provide only short-term relief and desensitisation involves the use of the actual allergen, which can result in potentially frequent harmful side-effects. The possibility of anaphylaxis is never completely eliminated in patients suffering from allergic diseases and this causes a great deal of stress to the patient and their families.

The present inventor submits that it would be desirable to develop an immunotherapeutic approach which involves safer use of an allergen, as lower doses may be employed, and provides longer-term protection against the allergic reaction. Since allergy results from over-reactivity of Th2/Th17 cells and a corresponding lack of activity of the Th1 response, a medication that is able to modify and balance a misdirected Th2/Th17 response would be beneficial in preventing the allergic reaction. Such a medication would further be suitable to treat diseases and conditions where an exaggerated Th17 response plays a role, such as IBD.

SUMMARY OF THE INVENTION

Following extensive experimentation, the present inventor has made the surprising discovery that the administration of a specific interferon alpha (IFN-α) subtype selected from IFN-α10, IFN-α14 and a hybrid thereof with a vaccine, for example comprising an allergen, can result in enhanced activation of the Th1 immune response and suppression of the Th2/Th17 immune response, this leading to the identification by the inventor of improved therapeutic compositions which have utility in the treatment and/or prophylaxis of allergy and allergic diseases and diseases and conditions where an exaggerated Th17 response plays a role. In particular, the inventor has identified that the administration of at least one food allergen which is capable of mediating a Th2/Th17 immune response with IFN-α10, IFN-α14 or a hybrid thereof can be used in the treatment of food allergy and associated allergic diseases.

According to a first aspect of the present invention, there is provided a method for the treatment and/or prophylaxis of a condition where an enhancement of a Th1-mediated immune response and suppression of a Th2/Th17-mediated immune response are desired, said method comprising the step of:

(i) administering to a subject in need thereof a therapeutically effective amount of at least one interferon alpha subtype selected from IFN-α10, IFN-α14 and a hybrid thereof.

In certain embodiments, the method includes a step of administering to the subject a therapeutically effective amount of a vaccine composition for treatment or prophylaxis of the condition where an enhancement of a Th1- mediated immune response and suppression of a Th2/Th17-mediated immune response are desired. The vaccine composition may be administered sequentially, separately or simultaneously with the at least one interferon alpha subtype.

In certain embodiments, the vaccine composition comprises at least one antigen. In certain embodiments, the vaccine composition comprises at least one allergen capable of mediating a Th2/Th17 immune response, for example, a food allergen. In certain embodiments, the method therefore includes a step of administering to the subject a therapeutically effective amount of at least one allergen capable of mediating a Th2/Th17 immune response, for example, a food allergen. The allergen may be administered sequentially, separately or simultaneously with the at least one interferon alpha subtype.

Typically, the subject is a mammal, in particular a human. In certain embodiments, the subject is suffering from a condition where an enhancement of a Th1-mediated immune response and suppression of a Th2/Th17-mediated immune response are desired.

According to a second aspect of the present invention, there is provided at least one interferon alpha subtype selected from IFN-α10, IFN-α14 and a hybrid thereof for use in the treatment and/or prophylaxis of a condition where an enhancement of a Th1-mediated immune response and suppression of a Th2/Th17-mediated immune response are desired.

In certain embodiments, the at least one interferon alpha subtype is provided for simultaneous, separate or sequential administration with a vaccine composition for treatment or prophylaxis of the condition where an enhancement of a Th1-mediated immune response and suppression of a Th2/Th17-mediated immune response are desired. In certain embodiments, the at least one interferon alpha subtype is provided for simultaneous, separate or sequential administration with at least one allergen capable of mediating a Th2/Th17 immune response there against, for example, a food allergen.

According to a third aspect of the present invention, there is provided use of at least one interferon alpha subtype selected from IFN-α10, IFN-α14 and a hybrid thereof in the preparation of a medicament for the treatment and/or prophylaxis of a condition where an enhancement of a Th1-mediated immune response and suppression of a Th2/Th17-mediated immune response are desired.

In certain embodiments, the at least one interferon alpha subtype is provided for simultaneous, separate or sequential administration with a vaccine composition for treatment or prophylaxis of the condition where an enhancement of a Th1-mediated immune response and suppression of a Th2/Th17-mediated immune response are desired. In certain embodiments, the at least one interferon alpha subtype is provided for simultaneous, separate or sequential administration with at least one allergen capable of mediating a Th2/Th17 immune response there against, for example, a food allergen.

According to a further aspect of the present invention, there is provided a composition comprising:
(i) a vaccine for treatment or prophylaxis of a condition where an enhancement of a Th1-mediated immune response and suppression of a Th2/Th17-mediated immune response are desired; and
(ii) at least one interferon alpha subtype selected from IFN-α10, IFN-α14 and a hybrid thereof.

In certain embodiments, the vaccine comprises at least one allergen capable of mediating a Th2/Th17 immune response, for example, a food allergen.

A further aspect of the present invention provides a pharmaceutical composition for enhancement of a Th1 mediated immune response and suppression of a Th2/Th17-mediated immune response, wherein the composition comprises a vaccine for treatment or prophylaxis of a condition where an enhancement of a Th1-mediated immune response and suppression of a Th2/Th17-mediated immune response are desired and at least one interferon alpha subtype selected from IFN-α10, IFN-α14 and a hybrid thereof, along with a pharmaceutically acceptable excipient, diluent or carrier.

In certain embodiments, the vaccine comprises at least one allergen capable of mediating a Th2/Th17 immune response, for example, a food allergen.

In a further aspect, the present invention extends to improvements in the efficacy of vaccines, for example, anti-allergy or allergic disease vaccines. A composition which comprises a vaccine for treatment or prophylaxis of a condition where an enhancement of a Th1-mediated immune response and suppression of a Th2/Th17-mediated immune response are desired, such as at least one allergen capable of mediating a Th2/Th17 immune response, and at least one interferon alpha subtype selected from IFN-α10, IFN-α14 and a hybrid thereof has been surprisingly identified by the inventor as providing an unexpectedly efficacious composition for the treatment and/or prophylaxis of diseases, such as allergy or associated allergic diseases.

Accordingly, a further aspect of the present invention provides a vaccine composition comprising;
(i) a vaccine for treatment or prophylaxis of a condition where an enhancement of a Th1-mediated immune response and suppression of a Th2/Th17-mediated immune response are desired; and
(ii) at least one interferon alpha subtype selected from IFN-α10, IFN-α14 and a hybrid thereof.

In certain embodiments, the vaccine comprises at least one allergen capable of mediating a Th2/Th17 immune response, for example, a food allergen.

A further aspect of the present invention provides a vaccine composition for use in the treatment and/or prophylaxis of allergy, where an enhancement of a Th1-mediated immune response and the suppression of a Th2/Th17-mediated immune response are desired, said vaccine composition comprising;
(i) at least one allergen capable of mediating a Th2/Th17 immune response; and
(ii) at least one interferon alpha subtype selected from IFN-α10, IFN-α14 and a hybrid thereof.

A further aspect of the present invention provides for the use of a vaccine composition comprising at least one allergen capable of mediating a Th2/Th17 immune response and at least one interferon alpha subtype selected from IFN-α10, IFN-α14 and a hybrid thereof in the preparation of a medicament for the treatment and/or prophylaxis of allergy or associated allergic diseases.

A further aspect of the present invention provides a method for the treatment and/or prophylaxis of allergy or associated allergic diseases, the method comprising the step of:
(i) administering a therapeutically effective amount of a vaccine composition or an immunogenic composition which comprises at least one allergen capable of mediating a Th2/Th17 immune response and at least one interferon alpha subtype selected from IFN-α10, IFN-α14 and a hybrid thereof to a subject in need thereof.

According to a further aspect of the present invention, there is provided a method for the treatment and/or prophylaxis of a condition mediated by enhanced expression of IL17, said method comprising the step of:
(i) administering to a subject in need thereof a therapeutically effective amount of at least one interferon alpha subtype selected from IFN-α10, IFN-α14 and a hybrid thereof.

According to a further aspect of the present invention, there is provided at least one interferon alpha subtype selected from IFN-α10, IFN-α14 and a hybrid thereof for use in the treatment and/or prophylaxis of a condition mediated by enhanced expression of IL17.

According to a further aspect of the present invention, there is provided use of at least one interferon alpha subtype selected from IFN-α10, IFN-α14 and a hybrid thereof in the preparation of a medicament for the treatment and/or prophylaxis of a condition mediated by enhanced expression of IL17.

According to a further aspect of the present invention, there is provided a method for modulating an immune response, said method comprising the step of:
(i) administering to a subject in need thereof a therapeutically effective amount of at least one interferon alpha subtype selected from IFN-α10, IFN-α14 and a hybrid thereof.

According to a further aspect of the present invention, there is provided at least one interferon alpha subtype selected from IFN-α10, IFN-α14 and a hybrid thereof for use in modulating an immune response.

According to a further aspect of the present invention, there is provided use of at least one interferon alpha subtype selected from IFN-α10, IFN-α14 and a hybrid thereof in the preparation of a medicament for modulating an immune response.

In certain embodiments of the aspects of the invention outlined above, the at least one interferon alpha subtype is provided for simultaneous, separate or sequential administration with a vaccine for treatment or prophylaxis of the condition where an enhancement of a Th1-mediated immune response and suppression of a Th2/Th17-mediated immune response are desired, for example, a vaccine for the treatment or prophylaxis of a condition mediated by enhanced expression of IL17, e.g. an inflammatory disease or condition or an autoimmune disease, such as inflammatory bowel disease (IBD), ulcerative colitis (UC) or Crohn's disease (CD). In certain embodiments, the vaccine composition comprises at least one antigen. In certain embodiments, the vaccine comprises at least one allergen capable of mediating a Th2/Th17 immune response there against, for example, a food allergen.

In certain embodiments of the aspects of the invention outlined above, the at least one IFN-α subtype comprises, consists of or is IFN-α10. In certain embodiments, the at least one IFN-α subtype comprises, consists of or is IFN-α14. In certain embodiments, the at least one IFN-α subtype comprises, consists of or is a hybrid of IFN-α10 and IFN-α14, such as a fusion protein, or the like. In certain embodiments, the at least one IFN-α subtype comprises, consists of or is a recombinant form of IFN-α10 and/or IFN-α14.

In certain embodiments of the aspects of the invention outlined above, the at least one allergen is at least one food allergen. In certain embodiments, the at least one allergen is a dietary allergen such as food, an environmental allergen such as the venom of stinging insects, or a medication.

In certain embodiments of the aspects of the invention outlined above, the at least one food allergen is selected from the group consisting of, but not limited to, corn, garlic, oats, coffee, chocolate, pickle, wheat or gluten and their products or derivatives which include durum wheat, spelt (*triticum spelta*), kamut (*triticum* poloncium), couscous, bran, wheat bran, wheat germ, wheat gluten, farina, rusk, semolina, durum wheat semolina, flour, wholewheat flour, wheat flour, wheat starch, starch, modified starch, hydrolysed starch, food starch, edible starch, vegetable starch, vegetable gum, vegetable protein, cereal filler, cereal binder, cereal protein; tree nuts (including almonds, cashews, macademia, walnut and brazil nuts); seeds, including sesame, sunflower and poppy seeds; dairy derived antigens, such as milk or milk derivatives, including cheese and yoghurt; fish or shellfish or their derivatives, including from the mollusc phylum (gastropod class: snails and abalone; bivalve class: clam, mussel and oyster; cephalopod class: octopus, squid and scallop), arthropod phylum (crustacean family: crab, lobster, shrimp, prawn and crayfish) or chordate phylum (cartilaginous family: ray and shark; bony fish: cod, salmon and tuna); eggs or egg derivatives; monosodium glutamate (MSG); sulphites or sulphur dioxide; legume allergies to the leguminosae family, which includes peanut, soya (soybean or soya derivatives), bean seeds, peas, green beans, lentils, carob and liquorice; other vegetable allergies such as potato; fruit allergies to the rosaceae family, which includes apple, pear, cherry, peach and plum; fruit allergies to the cucurbitaceae family, which includes cucumber, melon, watermelon, zucchini and pumpkin; and other fruit allergies such as those developed against kiwi, banana, avocado, tomatoes, strawberries and raspberries.

In certain embodiments, the vaccine or vaccine composition is a vaccine composition for the treatment or prophylaxis of a condition mediated by enhanced expression of IL17, e.g. an inflammatory disease or condition or an autoimmune disease, such as inflammatory bowel disease (IBD), ulcerative colitis (UC) or Crohn's disease (CD). In certain embodiments, the vaccine or vaccine composition is a vaccine composition for the treatment or prophylaxis of an inflammatory disease or condition or an autoimmune disease, such as inflammatory bowel disease (IBD), ulcerative colitis (UC) or Crohn's disease (CD).

In certain embodiments of the aspects of the invention outlined above, the condition where an enhancement of a Th1-mediated immune response and the suppression of a Th2/Th17-mediated immune response are desired is a condition mediated by enhanced expression of IL17, e.g. an inflammatory disease or condition or an autoimmune disease, such as inflammatory bowel disease (IBD), ulcerative colitis (UC) or Crohn's disease (CD).

In certain embodiments of the aspects of the invention outlined above, the condition where an enhancement of a Th1-mediated immune response and the suppression of a Th2/Th17-mediated immune response are desired is an inflammatory disease, in particular an inflammatory disease which is mediated by an exaggerated or overactive Th17 immune response. In certain embodiments of the aspects of the invention outlined above, the condition where an enhancement of a Th1-mediated immune response and the suppression of a Th2/Th17-mediated immune response are desired is an autoimmune disease, in particular an autoimmune disease which is mediated by an exaggerated or overactive Th17 immune response. For example, in certain embodiments the condition is inflammatory bowel disease (IBD), such as ulcerative colitis (UC) or Crohn's disease (CD). In certain embodiments, the condition is selected from the group consisting of asthma, allergic rhinitis, atopic dermatitis and food allergy.

In certain embodiments of the aspects of the invention outlined above, the condition where an enhancement of a Th1-mediated immune response and the suppression of a Th2/Th17-mediated immune response are desired is an allergy or associated allergic diseases and conditions caused thereby. In particular, in certain embodiments the condition is a food allergy including food associated or derived allergies and associated allergic diseases and conditions caused thereby.

In certain embodiments, the food allergy associated allergic diseases or conditions include, but are not limited to, milk/dairy allergy, including Heiner syndrome, egg allergy, soya allergy, fish (shellfish) allergy, peanut and tree nut allergy, sesame and other seed allergy, wheat and grains allergy, fruit and vegetable allergy, caffeine allergy, oral allergy syndrome, alcohol allergy, pollen food allergy syndrome, eosinophilic gastroenteritis, IgE mediated gastrointestinal food allergy and C1 esterase deficiency.

In certain embodiments of the present invention, the method of administration is oral administration. In certain embodiments, the method of administration is sublingual or buccal administration. In certain embodiments, the method of administration involves placing a lozenge under the patient's tongue. In certain embodiments, the route of administration is ocular or by means of introduction into the nasal cavity, by way of nasal administration. Also it may be introduced by oral administration (swallowing) of a capsule or similar device into the small intestine/duodenum such that the capsule does not dissolve in the stomach, but bypasses same and delivers/releases the interferon alpha subtype only into the small intestine/duodenum.

DETAILED DESCRIPTION OF THE INVENTION

The inventor of the present invention has surprisingly discovered that administering an IFN-α subtype selected from IFN-α10, IFN-α14 and a hybrid thereof results in the enhancement of a Th1 T cell mediated immune response and the suppression of a Th2/Th17 T cell mediated immune response and can therefore skew the immune response towards a cell-mediated (Th1) path, whilst simultaneously suppressing the allergic (Th2/Th17) response. Surprisingly, this effect is enhanced when the IFN-α subtype is administered orally. This finding can be applied to provide an improved method and improved adjuvant composition for treating and/or preventing conditions where the enhancement of a Th1 T cell mediated immune response and/or the suppression of a Th2/Th17 T cell mediated immune response are desired, for example, inflammatory, autoimmune or allergy conditions. In particular, IFN-α10, IFN-α14 or a hybrid thereof may be used as adjuvants in vaccines to boost immune response to antigens and direct the immune response towards a Th1 immune response.

The inventor has also discovered that a combination of a vaccine composition or a food allergen which is capable of mediating a Th2/Th17 immune response and an IFN-α subtype selected from IFN-α10, IFN-α14 and a hybrid thereof can result in the activation of a Th1 T cell mediated immune response and the suppression of a Th2/Th17 T cell mediated immune response. In particular, the inventor has surprisingly discovered that orally administering the combination can result in the activation of a Th1 T cell mediated immune response and the suppression of a Th2/Th17 T cell mediated immune response. A standard flu vaccine was mixed with a low dose of leukocyte derived interferon alpha (LDA1) and orally administered to mice. The inventor noted that without the interferon, a small anti-flu antibody response was recorded in mice, which was approximately 50 times less than with an injected vaccine. With interferon-alpha, the response from the orally delivered vaccine was exactly the same as the injected vaccine. A series of buccal immunisations using a standard protein antigen and two interferons, LDA1 and an isolated subtype IFN-α14, surprisingly resulted in oral immunisation of mice to which the composition was administered. However, the inventor surprisingly noted that while the LDA1 gave a balanced response, IFN-α14 mediated only a significant humoral response. The production of IgG1 is indicative of a Th2 response (humoral immunity) and the production of IgG2a is indicative of a Th1 response (cell-mediated immunity).

The inventor, whilst not wishing to be bound by theory, has identified that the oral administration of a food allergen capable of mediating a Th2/Th17 immune response and an interferon alpha subtype selected from IFN-α10 and IFN-α14 can skew the immune response towards a cell-mediated (Th1) path, whilst simultaneously suppressing the allergic (Th2/Th17) response. Accordingly, the inventor has surprisingly shown for the first time that the co-administration of an allergen such as a food derived antigen that is causative of allergy or associated allergic diseases in a subject with certain interferon subtypes modulates the resulting immune response and skews it away from the Th2/Th17 response which would have been expected to develop against the allergen or antigen. This surprising finding provides an unexpected approach to treat or prevent allergic responses or diseases which occur in subjects as a result of allergens such as food derived allergens.

DEFINITIONS

Subject

As herein defined, a "subject" includes and encompasses mammals such as humans, primates and livestock animals (e.g. sheep, pigs, cattle, horses, donkeys); laboratory test animals such as mice, rabbits, rats and guinea pigs; and companion animals such as dogs and cats.

Treatment/Therapy

The term "treatment" is used herein to refer to any regimen that can benefit a human or non-human animal. The treatment may be in respect of any existing inflammatory, autoimmune, allergic or allergy associated condition and the treatment may be prophylactic (preventative treatment). Treatment may include curative or alleviative effects. Reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition. Accordingly, therapeutic and/or prophylactic treatment includes amelioration of the symptoms of a particular allergic condition or preventing or otherwise reducing the risk of developing a particular allergic condition. The term "prophylactic" may be considered as reducing the severity or the onset of a particular condition. "Therapeutic" may also reduce the severity of an existing condition.

Administration

The active ingredients used in the present invention (e.g. vaccine or allergen and IFN-α10, IFN-α14 or a hybrid thereof) can be administered separately to the same subject, optionally sequentially, or can be co-administered simultaneously as a pharmaceutical, immunogenic or vaccine composition. In certain embodiments, the vaccine or allergen is co-administered with the interferon alpha subtype. The pharmaceutical composition will generally comprise a suitable pharmaceutical excipient, diluent or carrier selected depending on the intended route of administration.

The active ingredients can be administered to a patient in need of treatment via any suitable route. The precise dose will depend upon a number of factors, as is discussed below in more detail.

One suitable route of administration is parenterally (including subcutaneous, intramuscular, intravenous, by means of, for example a drip patch). Other suitable routes of administration include (but, are not limited to) oral, ocular, nasal, topical (including buccal and sublingual), infusion, intradermal or administration via oral or nasal inhalation, by means of, for example, a nebuliser or inhaler, or by an implant. Preferable routes of administration include (but, are not limited to) oral, buccal and sublingual. The compositions of the invention may also be administered in such a manner that they are directed to, or released in, specific areas of the gut intestinal tract (such as the small intestine/duodenum). Typically such release will occur after passage through the stomach, this targeted release being achievable through the use of coatings and the like.

For intravenous injection, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, Lactated Ringer's injection. Preservatives, stabilisers, buffers, antioxidants and/or other additives may be included, as required.

The compositions of the present invention for oral administration may be in tablet, capsule, lozenge, powder or liquid form. Oral administration may involve placing a lozenge under the tongue of the patient. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The compositions of the present invention may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. 7th Edition ISBN 0-683305-72-7, the entire disclosures of which are herein incorporated by reference.

Pharmaceutical Compositions

As described above, the present invention extends to a pharmaceutical composition for the treatment of inflammatory diseases, autoimmune diseases and allergy such as food allergy and associated allergic diseases and, in particular, for the induction of a Th1 immune response and the suppression or inhibition of a Th2/Th17 immune response.

Pharmaceutical compositions according to the present invention, and for use in accordance with the present invention, may comprise, in addition to an active ingredient, a pharmaceutically acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be, for example, oral, intravenous, intranasal or via oral or nasal inhalation. The formulation may be a liquid, for example, a physiologic salt solution containing non-phosphate buffer at pH 6.8-7.6, or a lyophilised or freeze-dried powder.

Dose

The composition is preferably administered to an individual in a "therapeutically effective amount" or a "desired amount", this being sufficient to show benefit to the individual. As defined herein, the term an "effective amount" means an amount necessary to at least partly obtain the desired response, or to delay the onset or inhibit progression or halt altogether the onset or progression of a particular condition being treated. The amount varies depending upon the health and physical condition of the subject being treated, the taxonomic group of the subject being treated, the degree of protection desired, the formulation of the composition, the assessment of the medical situation and other relevant factors. It is expected that the amount will fall in a relatively broad range, which may be determined through routine trials. Prescription of treatment, e.g. decisions on dosage etc, is ultimately within the responsibility and at the discretion of general practitioners, physicians or other medical doctors, and typically takes account of the disorder to be treated, the condition of the individual patient, the site of delivery, the method of administration and other factors known to practitioners. The optimal dose can be determined by physicians based on a number of parameters including, for example, age, sex, weight, severity of the condition being treated, the active ingredient being administered and the route of administration. A broad range of doses may be applicable. Considering oral administration to a human patient, for example, from about 10 μg to about 1000 μg of agent may be administered per human dose, optionally for 3 to 4 doses. Dosage regimes may be adjusted to provide the optimum therapeutic response and reduce side effects. For example, several divided doses may be administered daily, weekly, monthly or other suitable time intervals or the dose may be proportionally reduced as indicated by the exigencies of the situation.

Unless otherwise defined, all technical and scientific terms used herein have the meaning commonly understood by a person who is skilled in the art in the field of the present invention.

Autoimmune Disease

The term "autoimmune disease" as used herein is understood to mean any disease or condition which is caused by a body's tissues being attacked by its own immune system.

Throughout the specification, unless the context demands otherwise, the terms "comprise" or "include", or variations such as "comprises" or "comprising", "includes" or "including" will be understood to imply the inclusion of a stated integer or group of integers, but not the exclusion of any other integer or group of integers.

The present invention will now be exemplified with reference to the following non-limiting figures and examples which are provided for the purpose of illustration and are not intended to be construed as being limiting on the present

EXAMPLE 1

Identification of Interferon-Alpha Subtypes that are Immunological Adjuvants

50 µg ovalbumin and $10^5$ IU of interferon subtypes IFN-α14, IFN-α2, IFN-α21, IFN-α10, an IFN "mix" (including IFN-α1, IFN-α8, IFN-α21 and possibly IFN-α17), IFN-α8, Intron A, MULTIFERON™ and IFN-α1 in 50 µl were administered via intraperitoneal injection three times per week to BALB-c female mice, in groups of 10.

The serum concentrations of IgG1 mg/ml (Th2 response—humoral immunity to the ovalbumin antigen) and IgG2a mg/ml (Th1 response—cell-mediated immunity to the ovalbumin antigen) were measured by ELISA.

Figure 1:
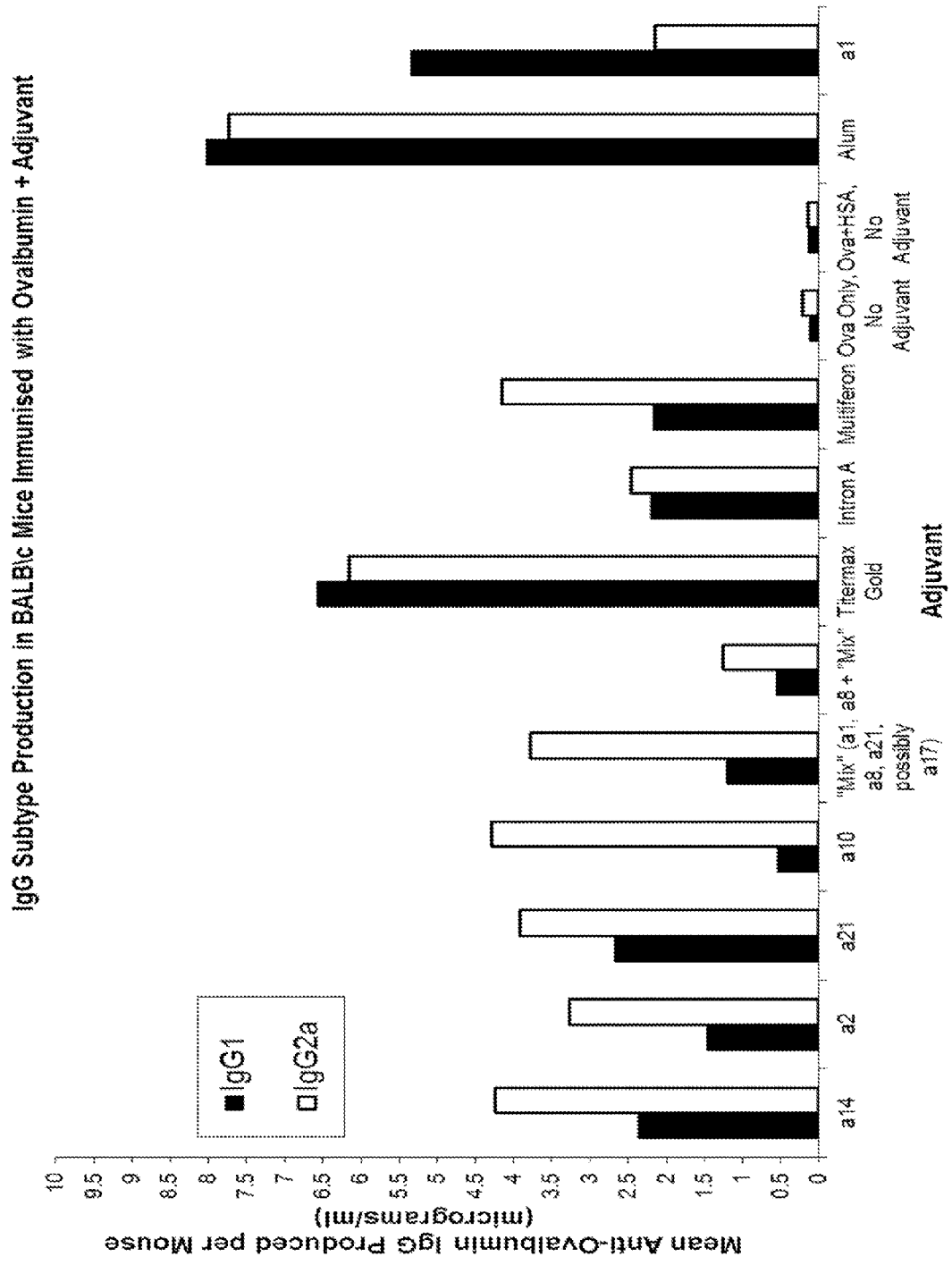
FIG. 1 shows a graph of IgG subtype (IgG1 and IgG2a) production in BALB-c mice immunised with ovalbumin and different subtypes of IFN-α.
Figure 2:
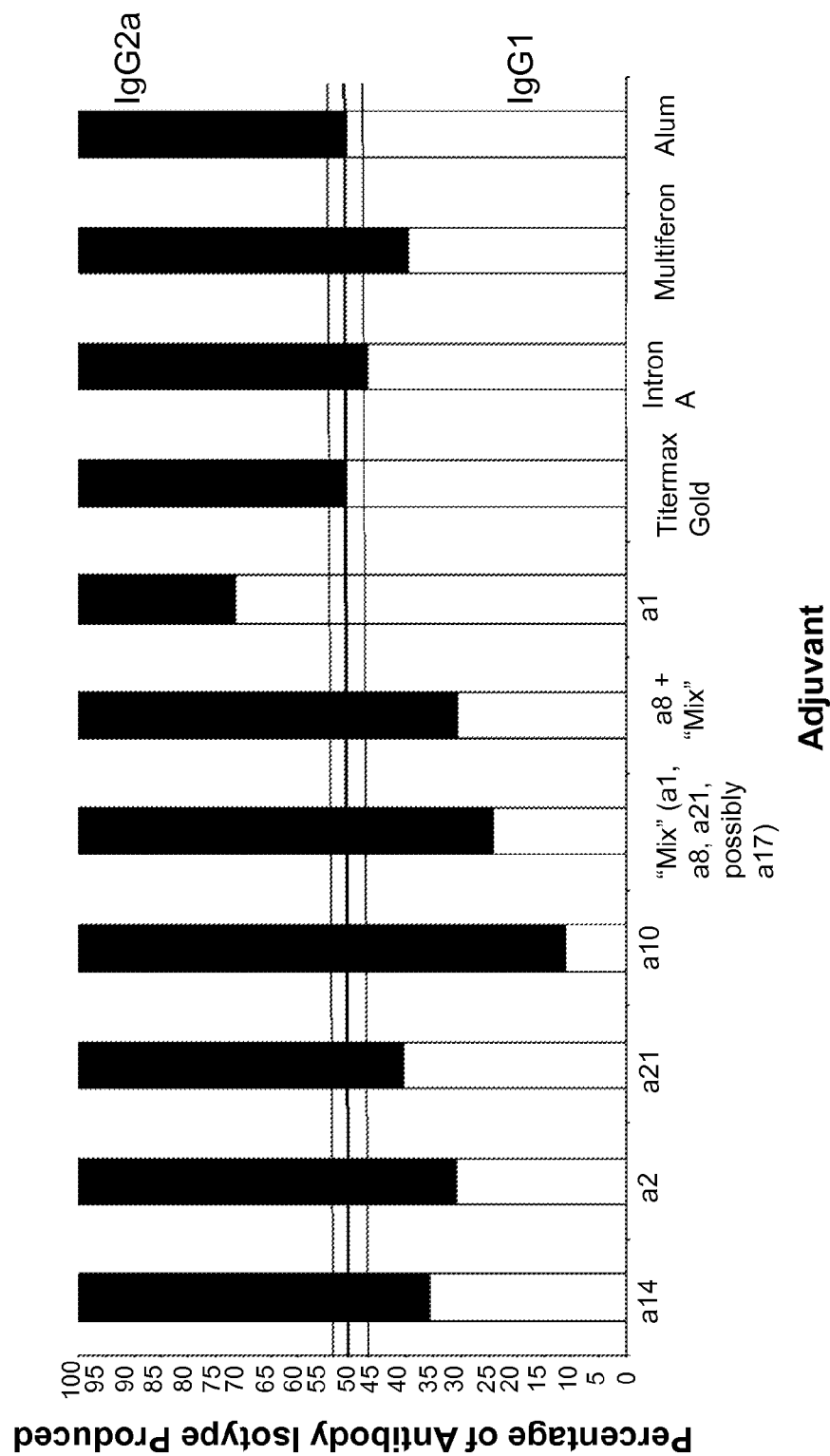
FIG. 2 shows a graph of the percentage of IgG subtype (IgG1 and IgG2a) produced in BALB-c mice immunised with ovalbumin and different subtypes of IFN-α.
Figure 3A:
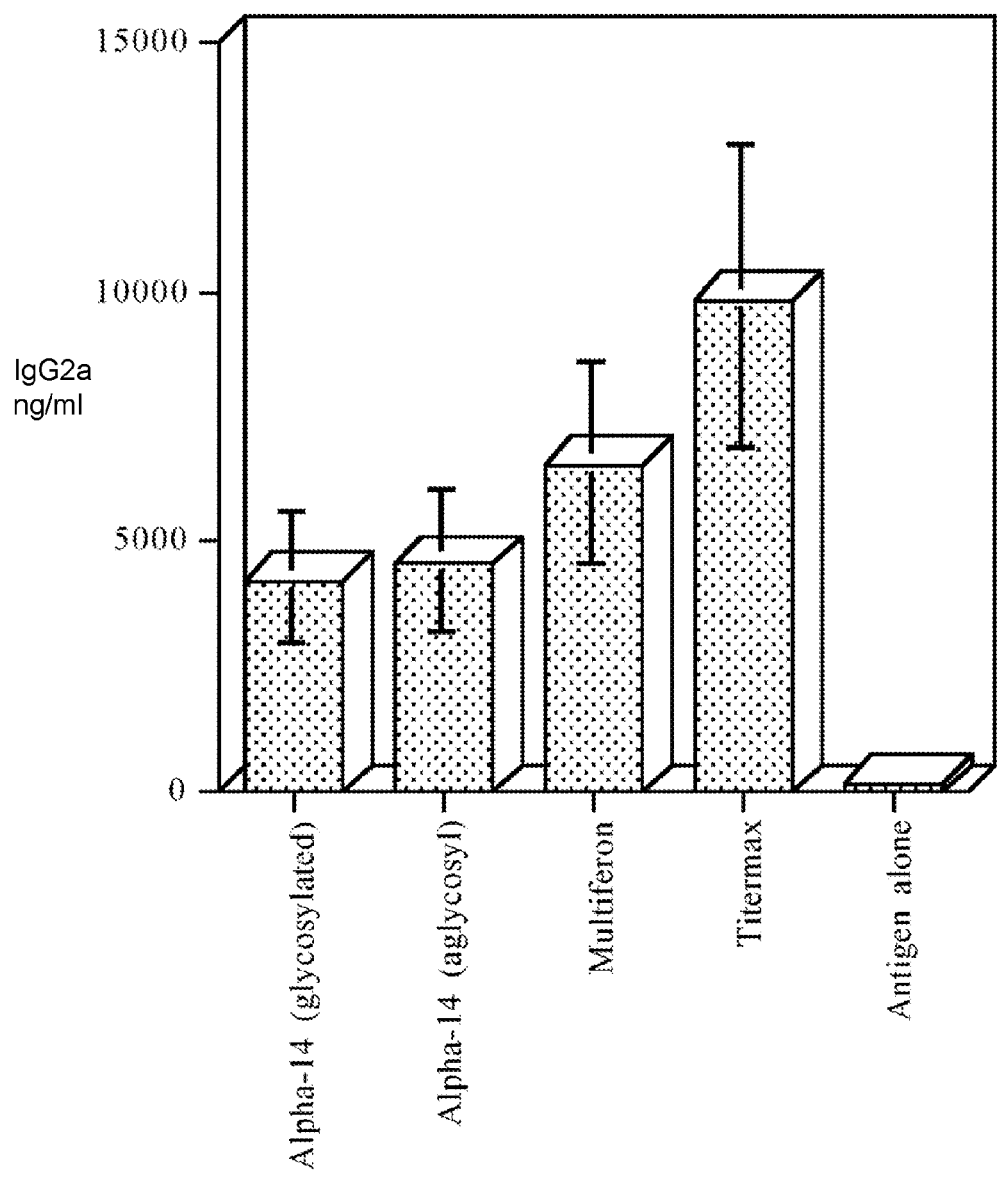
FIG. 3a shows a graph of IgG2a production in BALB-c mice immunised with ovalbumin and MULTIFERON™, glycosylated IFN-α14 and non-glycosylated IFN-α14 administered via intraperitoneal injection.
Figure 3B:
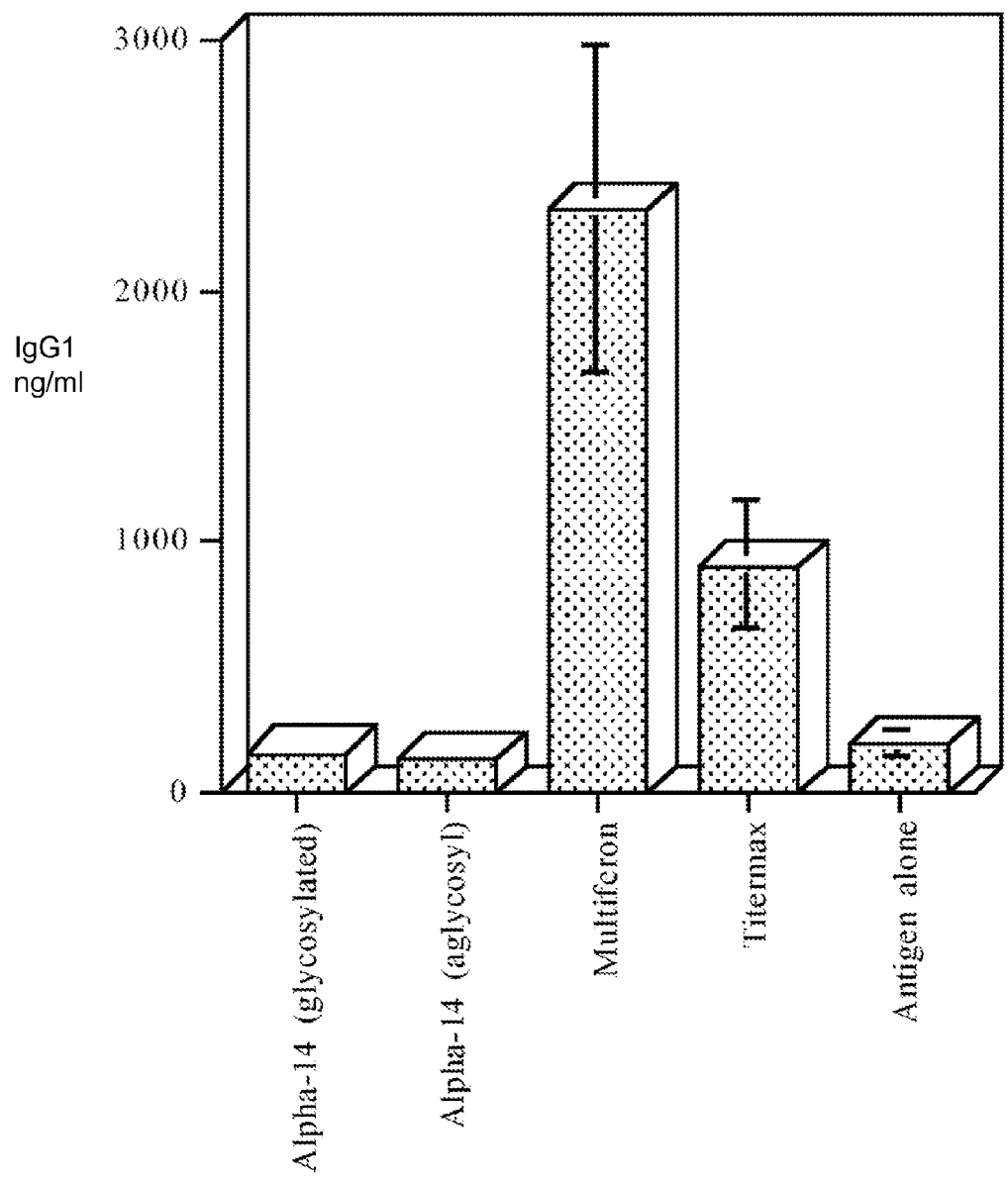
FIG. 3b shows a graph of IgG1 production in BALB-c mice immunised with ovalbumin and MULTIFERON™, glycosylated IFN-α14 and non-glycosylated IFN-α14 administered via intraperitoneal injection.
Figure 3C:
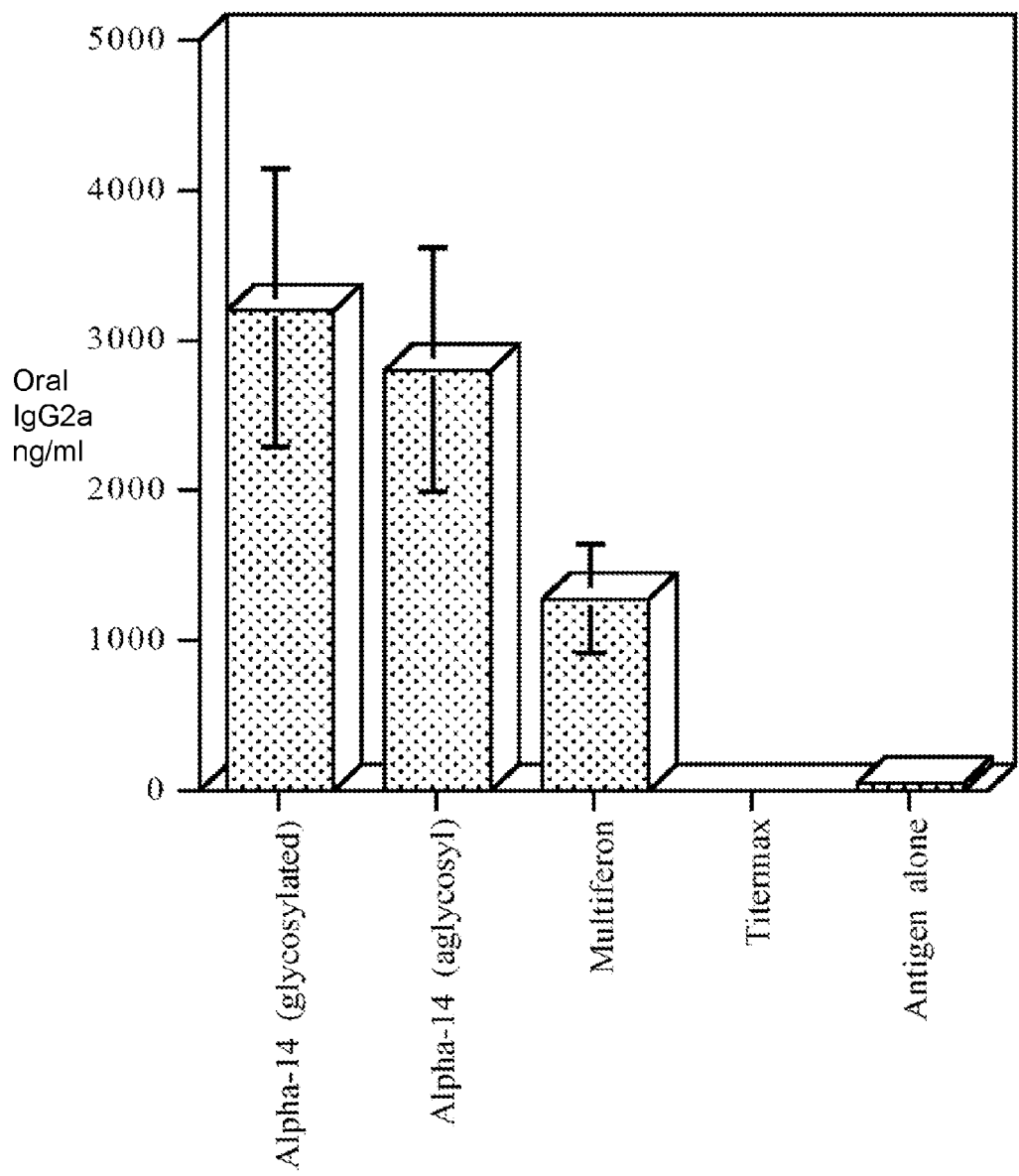
FIG. 3c shows a graph of IgG2a production in BALB-c mice immunised with ovalbumin and MULTIFERON™, glycosylated IFN-α14 and non-glycosylated IFN-α14 administered orally.
Figure 3D:
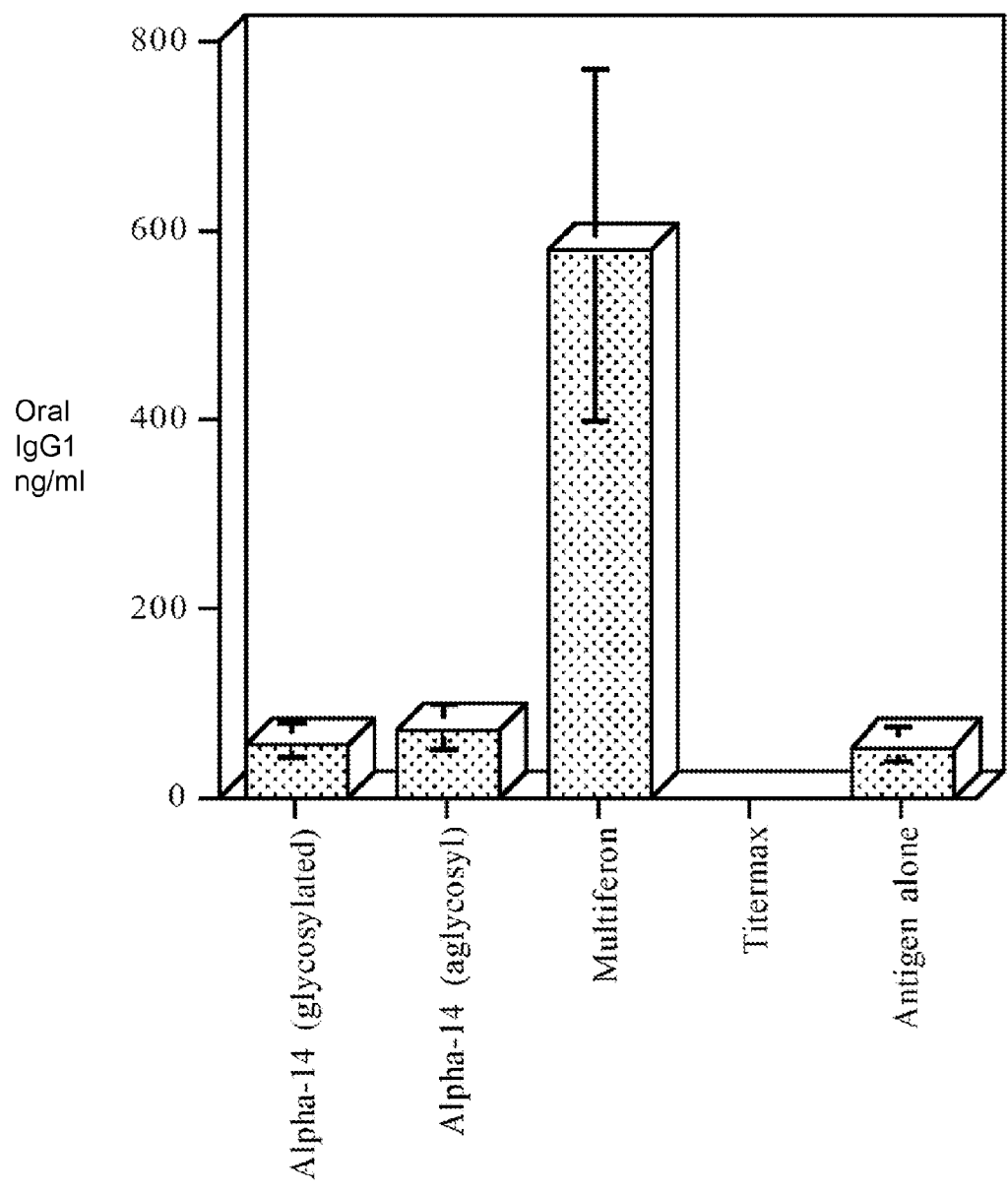
FIG. 3d shows a graph of IgG1 production in BALB-c mice immunised with ovalbumin and MULTIFERON™, glycosylated IFN-α14 and non-glycosylated IFN-α14 administered orally.

FIGS. 1 and 2 show the anti-ovalbumin IgG subtype production in BALB-c mice treated with IFN-α14, IFN-α2, INF-α21, IFN-α10, a "mix" of IFN-α1, IFN-α8, IFN-α21 and possibly IFN-α17), IFN-α8, Intron A, MULTIFERON™, ovalbumin only, ovalbumin plus human serum albumin (used as a carrier in interferon preparations) and IFN-α1.

The inventor demonstrated that IFN-α10 and IFN-α14 enhanced the production of IgG2a antibodies significantly which is indicative of an enhanced Th1 immune response. The inventor also demonstrated that IFN-α10 in particular showed low production of IgG1 antibody which is indicative of suppressing a Th2/Th17 immune response.

EXAMPLE 2

Identification of Antibody Response in BALB-c Mice after Administration of a Composition Comprising a Flu Vaccine and a Low Dose of Leukocyte Derived Interferon-Alpha (LDA1)

The standard flu vaccine was mixed with a low dose ($10^5$ IU) of leukocyte derived interferon alpha (LDA1). Without the interferon, a small anti-flu antibody response was recorded in mice, approximately 50 times less than with an injection. With interferon-alpha, the response from the orally delivered vaccine was exactly the same as the injected vaccine. A series of buccal immunisations were carried out using a standard protein antigen (ovalbumin). Two interferons were compared, namely, the LDA1 and an isolated subtype, IFN-α14. Both produced a remarkable oral immunisation of the mice, but whereas the LDA1 gave a balanced response, the IFN-α14 gave only a significant humoral response. The production of IgG1 is indicative of a Th2/Th17 response (humoral immunity) and the production of IgG2a is indicative of a Th1 response (cell-mediated immunity).

EXAMPLE 3

The Identification of IFN-Alpha as an Oral Immunological Adjuvant

50 µg ovalbumin and $10^5$ IU of interferon subtypes, namely MULTIFERON™, glycosylated IFN-α14 and non-glycosylated IFN-α14, in 50 µl doses were administered three times a week to BALB-c female mice via oral (buccal) and intraperitoneal injection administration.

The controls used were antigen alone and Titermax— Titermax is a mixture of compounds used in antibody generation and vaccination to stimulate the immune system to recognise an antigen given together with the mixture. Titermax is a recently developed immune adjuvant deemed to be safe in animals.

Serum concentrations (mg/ml) of IgG1 (indicative of a Th2/Th17 response) and IgG2a (indicative of a Th1 response) anti-ovalbumin antibodies were quantitated by ELISA.

The production of IgG2a and IgG1 antibodies when MULTIFERON™, glycosylated IFN-α14 and aglycosyl IFN-α14 (CHO cell-derived) were administered both orally and by injection were compared (see FIGS. 3a, 3b, 3c and 3d).

The inventor demonstrated that IFN-α14 showed pronounced immunological adjuvant activity both orally and by injection. No significant difference was seen between the glycosylated and non-glycosylated preparations.

The inventor also demonstrated that IFN-α14 only enhanced IgG2a production associated with Th1 responses by the oral route of administration. Hence IFN-α14 is an activator of cell-mediated immunity when administered orally.

MULTIFERON™ enhanced both IgG1 and IgG2a responses when administered both orally and by injection i.e. it induced both Th1 and Th2 responses significantly.

EXAMPLE 4

The Generation of an In-Vivo Animal Model of Food Allergy

Staphylococcal enterotoxin B (SEB) and ovalbumin (OVA; Grade V) will be obtained from Sigma-Aldrich, and whole peanut extract (WPE) prepared from unsalted uncooked peanuts by using 20 mmol/L Tris buffer, as previously described (Koppelman S. J., et. al.). Total protein concentration of WPE may be determined by the Pierce bicinchoninic acid (BCA) protein assay.

Four 8 week old female BALB/c mice or female C57Bl/6 mice will be housed under specific pathogen-free conditions and maintained on an OVA and peanut-free diet. Mice will be administered 100 mg of OVA and various concentrations of SEB in a final volume of 100 mL by using a ball-ended mouse feeding needle once a week for 8 weeks. Sensitisation to WPE will be performed by using 100 mg WPE combined with 10 mg of SEB.

At week 9, all mice will receive a bolus challenge with oral antigen (5 mg). Symptom scoring will be performed in a blind fashion by two independent investigators according to previously described parameters of symptoms for determining IgE-mediated responses in murine food allergy (Li X. M. et. al.). Briefly, 0 is assigned if no symptoms are evident, and 1 to 5 are assigned if symptoms are observed, where 1 represents mild scratching, rubbing, or both, of the nose, head, or feet;
2 and 3 represent intermediate symptoms (e.g., edema around the eyes or mouth, pillar erection, and/or labored breathing);
4 represents significantly reduced motility, tremors, and/or significant respiratory distress; and
5 represents death.

One hour later, mice will be bled for plasma histamine levels. Twenty-four hours later, mice can be terminated and tissues collected for analysis. Blood pressure will be determined in groups of three SEB/OVA-sensitized BALB/c mice that may be placed in a Coda 1 noninvasive blood pressure system (Kent Scientific, USA) for 5 minutes to establish baseline parameters. The mice will then be challenged with 5 mg OVA or PBS, and parameters measured every 30 seconds.

Tests
Serum Immunoglobulin Levels

Serum will be collected and specific antibody levels determined by means of sandwich ELISA. OVA-specific IgG1, IgG2a, and IgE levels will be quantified. SEB-specific IgE levels will be determined by using biotin-labeled SEB as a secondary reagent to detect IgE captured with anti-IgE. WPE-specific IgE levels will be determined by coating ELISA plates with 1 mg/mL WPE and detecting bound antigen-specific immunoglobulins with isotype-specific antibodies available from BD Pharmingen.

Blood Eosinophil Quantification

Blood will be collected into EDTA-coated tubes, and absolute eosinophil numbers will be determined after staining with Discombe fluid.

Cytokine Production

Single-cell suspensions of splenocytes will be prepared and cultured for 48 hours at a concentration of 2-3 $10^6$ ml in the presence or absence of OVA (100 mg/ml) or WPE (1 mg/ml). Additionally, separate cultures can be prepared on anti-mouse CD3e (BD Pharmingen)-coated plates (1 mg/mL). Cytokine concentrations in the culture supernatants will be determined by using mouse Th1/Th2 Cytometric Bead Array (CBA) assays available from BD Pharmingen. The limit of detection is less than 2 pg/ml for each cytokine.

Histology

Tissue will be collected, fixed in formalin, and then embedded in paraffin and stained with hematoxylin and eosin or pinacyanol erythrosinate for mast cells by Histo-Scientific Research Laboratories. Mast cell numbers and activation status may be determined by counting cells with dense metachromatic granules and compact shape compared with those with dispersed granules extending clearly outside the cell body. The average number of mast cells from 20 high-powered fields (3400× magnification) will be determined for each sample.

Plasma Histamine Levels

Plasma histamine levels will be determined by using an EIA kit available from Becton Dickenson, as per the manufacturer's instructions.

Observations

SEB administered with antigen is expected to result in immune responses to the antigen. Responses are expected to be highly Th2 polarised, and an oral challenge with antigen is expected to trigger anaphylaxis and local and systemic mast cell degranulation. SEB-driven sensitisation is expected to induce eosinophilia in the blood and intestinal tissues.

EXAMPLE 5

In Vitro Determination of the Inhibition of Humoral Immunity (Th2/Th17) by Interferon-Alpha Subtypes—Analysis of Th17 Lymphocytes and Interleukin 17

A total of $2\times10^6$ human PBMCs were stimulated with lipopolysaccharide (LPS) in the absence or presence of increasing concentrations of recombinant human alpha-IFN. Supernatants were collected after 24 hours and IL-17 concentrations measured by ELISA.

Human Cell Culture

Human peripheral blood was collected from healthy volunteers and peripheral blood mononuclear cells (PBMCs) were obtained by Lymphoprep gradient centrifugation (Pierce). For PBMC experiments, $2\times10^6$ PBMCs per ml were seeded in 24-well plates and stimulated with lipopolysaccharide (LPS) from *Escherichia coli* 055:B5 (Sigma) or $2\times10^6$ PBMCs per mL are seeded into 24-well plates and stimulated with 5 mg/mL plate-bound anti-CD3 (clone: UCHT1) and 2.5 mg/mL anti-CD28 (clone: CD28.2). Naive T cells (CD4+CD45RA) are obtained by magnetically labeling and depletion of non-helper T-cell and memory T-cells performed according to manufacturer's instructions (Miltenyi Biotec). A total of $1\times10^5$ naive T-cells were primed in 96-well flat bottom plates coated with anti-CD3 (clone UCHT1, 2.5 mg/mL) and with anti-CD28 (clone CD28.2, 2.5 mg/mL) antibodies. After 48 h of culture, 20 IU/mL recombinant human IL-2 (Peprotech) is added to the culture.

For human Th17 differentiation, cells are supplemented with neutralising anti-IL-4 and anti-IFNγ antibodies (both from Peprotech) and with 10 ng/mL recombinant IL-1β and 50 ng/mL recombinant IL-6 (both from Peprotech). Where required, recombinant human IFNα10/14 is added to the culture. After 5 days of culture, cells are washed, transferred into new plates and expanded until day 12 in the presence of 20 IU/mL recombinant IL-2.

ELISA and Intracellular Cytokine Staining

The IL-17 producing capacity of primed Th17 cells was assessed by stimulation with 0.1 ng/ml LPS or alternatively can be assessed by the stimulation of human cells with soluble 1 mg/mL anti-CD3 (clone: OKT3) and phorbol-12-13-dibutyrate (PdBu). Concentrations of human IL-17 in cell culture supernatants were determined using commercially available antibody pairs and protein standards (R&D Systems). Absorption was determined using an ELISA reader at 450 nm. For intracellular staining of mouse IFNγ and IL-17, T-cells are stimulated with PMA and ionomycin for 5 hours. Brefeldin A is added for the final 3 h of culture. Intracellular staining can be performed with a BD Cytofix/Cytoperm kit according to the manufacturer's instructions. Cells are incubated with fluorescein isothiocyanate-labeled anti-IFNγ (clone: XMG1.2, BD Pharmingen) and Alexa Fluor 647-labeled anti-mouse IL-17A (clone: eBio17B7, eBioscience). After washing, cells are immediately analysed using Fluorescence-activated cell sorting (FACS).

Results

Figure 4:
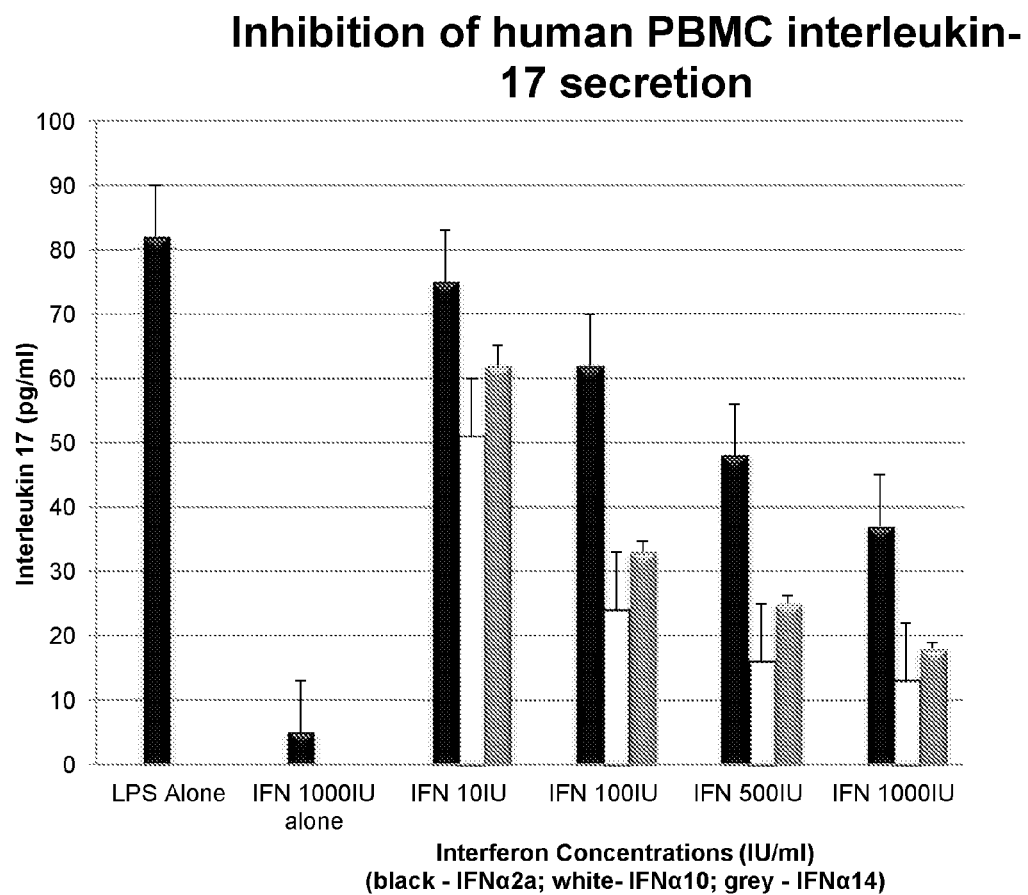
FIG. 4 shows inhibition of human PBMC interleukin-17 (IL17) secretion with lipopolysaccharide (LPS) alone and with LPS and increasing concentrations of IFN-α2a (black), IFN-α10 (white) or IFN-14 (grey).

IFNα10>IFNα14>IFNα2a. P<0.05 (FIG. 4).

EXAMPLE 6

In Vitro Determination of the Inhibition of Humoral Immunity (Th2/Th17) by Interferon-Alpha Subtypes—Analysis of Th2 Cells and Associated Cytokines CRTH2 Background CRTH2 (Chemoattractant Receptor-homologous molecule expressed on Th2 cells) is a G-protein coupled receptor expressed by Th2 lymphocytes, eosinophils, and basophils. The receptor mediates the activation and chemotaxis of these cell types in response to prostaglandin D2 (PGD2), the major prostanoid produced by mast cells. PGD2 is released through mast cell degranulation in the initial phase of IgE-mediated reactions. This process is also thought to occur at the site of inflammation, such as the nasal and bronchial mucosa. Through interaction with CRTH2, PGD2 is thought to mediate recruitment and activation of CRTH2-bearing cell types to the site of the allergic reaction, in consequence amplifying and maintaining the allergic inflammation. In the nasal and bronchial mucosa, this pro-inflammatory cascade is thought to start during the so-called late allergic response occurring 3 to 9 hours after allergen challenge. The interaction between PGD2 and CRTH2 would, therefore, contribute to the so-called "Th2 polarisation", with consequent Th2 cytokine production and the typical eosinophilic and basophilic characteristics of the inflammation.

IFNα Inhibits Human CD4+Th2 Development.

Purified human CD4+/CD45RA+ cells were activated with plate-bound anti-CD3/anti-CD28 under defined cytokine conditions. Induction of CRTH2 expression was assessed by flow cytometry. All P<0.05, above 100 IU IFN compared with IL-4 alone.

Human Subjects

Peripheral blood was collected from healthy adult donors and cells purified as below.

T Cell Cultures and Analysis

Peripheral blood was obtained from healthy male adult donors and naive CD4+/CD45RA+ T cells were purified (>92%) from buffy coats by magnetic bead separation (BD Biosciences, USA). CD4+ cells were activated with plate-bound anti-CD3/anti-CD28 and IL-2 (50 U/ml) in complete Iscove's Modified Dulbecco's Medium containing 10% FCS, in the presence of recombinant human recombinant IL-4 (R&D Systems, USA), at a concentration of 20 ng/ml for 7 days. Flow cytometric analysis was performed with hCD294 (chemo-attractant receptor homologous molecule expressed on Th2 cells [CRTH2])-Alexa 647 (BD Biosciences).

Results

Figure 5:
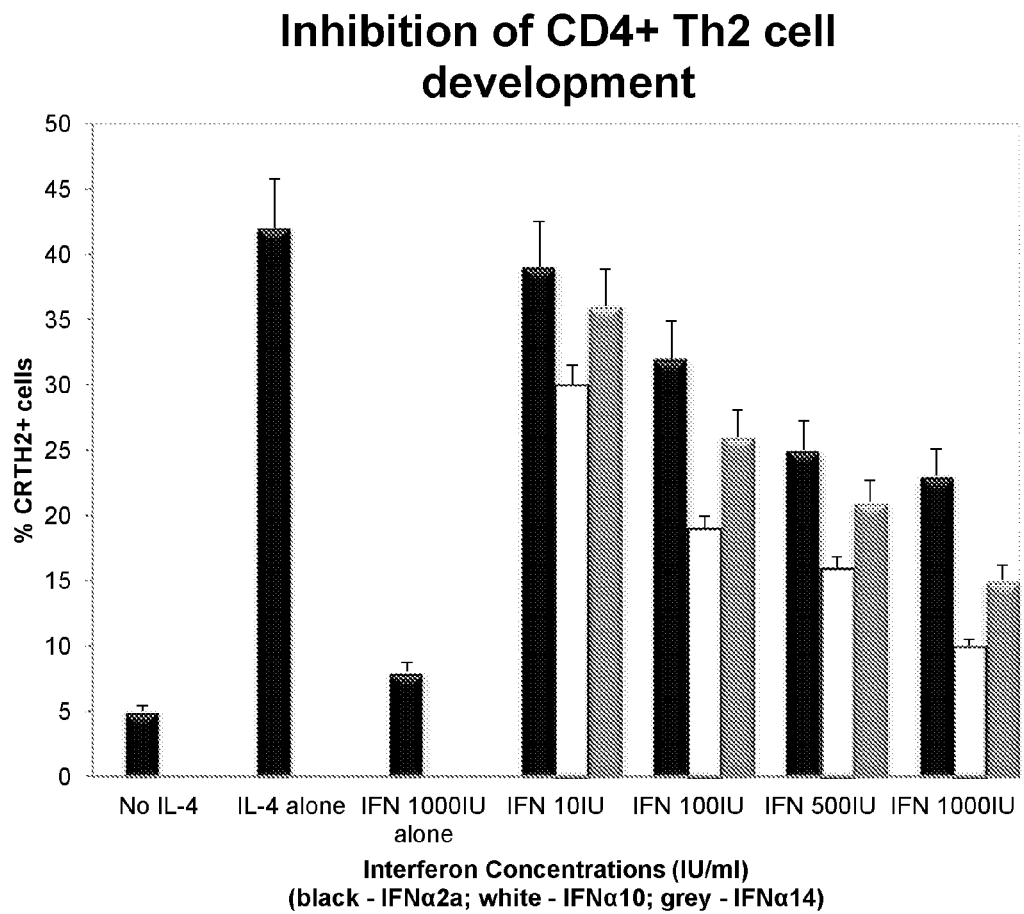
FIG. 5 shows the inhibition of Interleukin-4 (IL4)-induced CD4+Th2 cell development using increasing concentrations of IFN-α2a (black), IFN-α10 (white) or IFN-14 (grey).

In humans, the PGD2 receptor, CRTH2, is selectively expressed on Th2 cells and is induced by IL-4 during Th2 development. IL-4 promoted the development of cells expressing CRTH2. However, as shown in FIG. 5 all the IFN-alphas markedly blocked IL-4 driven CRTH2 expression, in a dose-dependent manner in the order IFNα10>IFNα14>IFNα2a, thus supporting the concept that these cytokines suppress Th2 (humoral) immunity, but are recognised as potent activators of Th1-associated immunity.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A method for the treatment of a condition where an enhancement of a Th1-mediated immune response and suppression of a Th2/Th17-mediated immune response are desired, said method comprising the step of:
   administering to a subject in need thereof, a therapeutically effective amount of at least one interferon alpha subtype selected from IFN-α10 and IFN-α14,
   wherein the condition where an enhancement of a Th1-mediated immune response and suppression of a Th2/Th17-mediated immune response are desired is selected from the group consisting of an autoimmune disease, an inflammatory disease and allergy or an associated allergic condition.

2. The method as claimed in claim 1 wherein the inflammatory disease is inflammatory bowel disease.

3. The method as claimed in claim 2 wherein the inflammatory bowel disease is ulcerative colitis or Crohn's disease.

4. The method as claimed in claim 1 wherein the condition where an enhancement of a Th1-mediated immune response and suppression of a Th2/Th17-mediated immune response are desired is allergy or an associated allergic condition.

5. The method as claimed in claim 4 wherein the allergy is food allergy or an associated allergic condition.

6. The method as claimed in claim 1 wherein the method includes a step of administering to the subject a therapeutically effective amount of a vaccine composition for treatment of the condition where an enhancement of a Th1-mediated immune response and suppression of a Th2/Th17-mediated immune response are desired.

7. The method as claimed in claim 6 wherein the vaccine composition comprises at least one allergen capable of mediating a Th2/Th17 immune response.

8. The method as claimed in claim 7 wherein the at least one allergen is a food allergen.

9. The method as claimed in claim 6 wherein the vaccine composition is administered sequentially, separately or simultaneously with the at least one interferon alpha subtype.

10. The method as claimed in claim 1 wherein the at least one interferon alpha subtype is administered orally.

11. The method as claimed in claim 1 wherein the at least one interferon alpha subtype is a recombinant form of IFN-α10 or IFN-α14.

12. A method for the treatment of a condition mediated by enhanced expression of IL17, said method comprising the step of:

administering to a subject in need thereof a therapeutically effective amount of at least one interferon alpha subtype selected from IFN-α10 and IFN-α14.

13. The method as claimed in claim 12 wherein the condition mediated by enhanced expression of IL17 is inflammatory bowel disease.

14. The method as claimed in claim 13 wherein the inflammatory bowel disease is ulcerative colitis or Crohn's disease.

15. The method as claimed in claim 12 wherein the at least one interferon alpha subtype is administered orally.

16. A method of treatment with an interferon alpha subtype, said method comprising the steps of:
    administering to a subject having a condition a therapeutically effective amount of at least one interferon alpha subtype selected from IFN-α10 and IFN-α14,
    wherein the condition is selected from the group consisting of an autoimmune disease, an inflammatory disease and allergy or an associated allergic condition; and
    wherein said treatment enhances a Th1-mediated immune response in the subject and suppresses a Th2/Th17-mediated immune response in the subject.

17. The method of claim 16 comprising a step of administering to the subject a therapeutically effective amount of a vaccine composition for treatment of the condition.

18. The method as claimed in claim 17 wherein the vaccine composition comprises at least one allergen capable of mediating a Th2/Th17 immune response.

19. The method as claimed in claim 18 wherein the at least one allergen is a food allergen.

20. The method as claimed in claim 17 wherein the vaccine composition is administered sequentially, separately or simultaneously with the at least one interferon alpha subtype.

21. The method as claimed in claim 16 wherein the at least one interferon alpha subtype is administered orally.

22. The method as claimed in claim 17 with the proviso that the vaccine does not include a viral antigen.

23. A composition comprising:
    i) a vaccine for treatment of a condition where an enhancement of a Th1-mediated immune response and suppression of a Th2/Th17-mediated immune response are desired, the condition being selected from the group consisting of an autoimmune disease, an inflammatory disease and allergy or an associated allergic condition; and
    ii) at least one interferon alpha subtype selected from IFN-α10 and IFN-α14.

24. The composition claimed in claim 23 wherein the vaccine comprises at least one allergen capable of mediating a Th2/Th17 immune response there against.

25. The composition as claimed in claim 24 wherein the at least one allergen is a food allergen.

26. The composition as claimed in claim 23 wherein the composition is provided for administration orally.

27. The composition as claimed in claim 23 wherein the at least one interferon alpha subtype is a recombinant form of IFN-α10 or IFN-α14.

28. The composition as claimed in claim 23, wherein the composition comprises said vaccine and said at least one interferon alpha subtype selected from IFN-α10 and IFN-α14, along with a pharmaceutically acceptable excipient, diluent or carrier.

* * * * *